(12) United States Patent
Creighton, IV

(10) Patent No.: US 6,975,197 B2
(45) Date of Patent: Dec. 13, 2005

(54) ROTATING AND PIVOTING MAGNET FOR MAGNETIC NAVIGATION

(75) Inventor: Francis M. Creighton, IV, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 145 days.

(21) Appl. No.: 10/056,227

(22) Filed: Jan. 23, 2002

(65) Prior Publication Data

US 2003/0137380 A1 Jul. 24, 2003

(51) Int. Cl.⁷ .............................. H01F 7/02
(52) U.S. Cl. ................ 335/306; 335/302; 335/296
(58) Field of Search ...... 335/216, 296–306; 600/9–15, 600/427, 400, 410; 324/318–322; 128/898–9

(56) References Cited

U.S. PATENT DOCUMENTS

| | | | |
|---|---|---|---|
| 5,257,636 A | | 11/1993 | White |
| 5,312,321 A | | 5/1994 | Holcomb |
| 5,622,169 A | | 4/1997 | Golden et al. |
| 5,667,469 A | * | 9/1997 | Zhang et al. ................... 600/9 |
| 5,681,260 A | | 10/1997 | Ueda et al. |
| 6,157,281 A | * | 12/2000 | Katznelson et al. ......... 335/306 |
| 6,241,671 B1 | * | 6/2001 | Ritter et al. ................. 600/427 |
| 6,304,768 B1 | * | 10/2001 | Blume et al. ................ 600/407 |
| 6,630,879 B1 | | 10/2003 | Creighton, IV et al. |

* cited by examiner

Primary Examiner—Lincoln Donovan
(74) Attorney, Agent, or Firm—Harness Dickey & Pierce PLC

(57) ABSTRACT

A magnet assembly comprising a magnet mounted for pivoting about a first axis spaced from the magnet, and rotating about a second axis that is perpendicular to and intersects with the first axis. The magnet comprising a plurality of segments each with a magnetization direction such that through a combination of pivoting and rotating the magnet projects a magnetic field in any direction at an operating point spaced from the front of the assembly. The segmented construction with segments of different magnetization directions allows small changes in the orientation of the magnet to substantially change the magnet field direction at a system operating point.

12 Claims, 12 Drawing Sheets

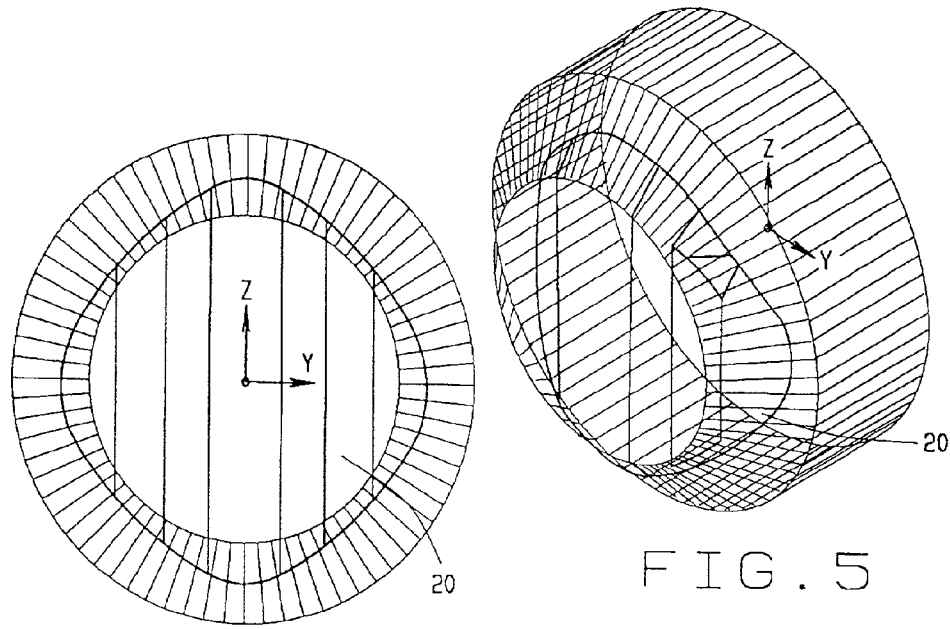
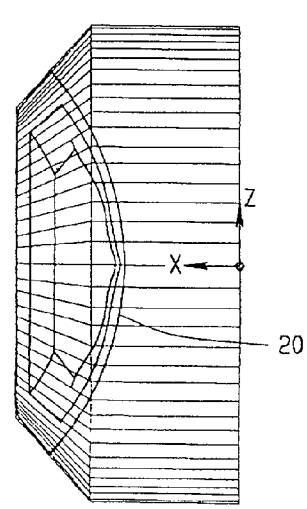
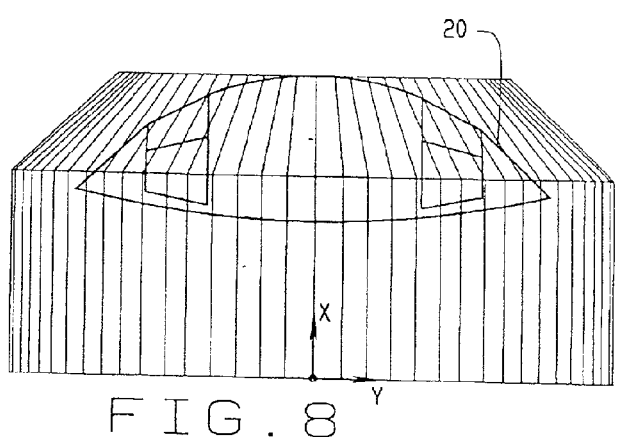
FIG.6
FIG.5
FIG.7
FIG.8

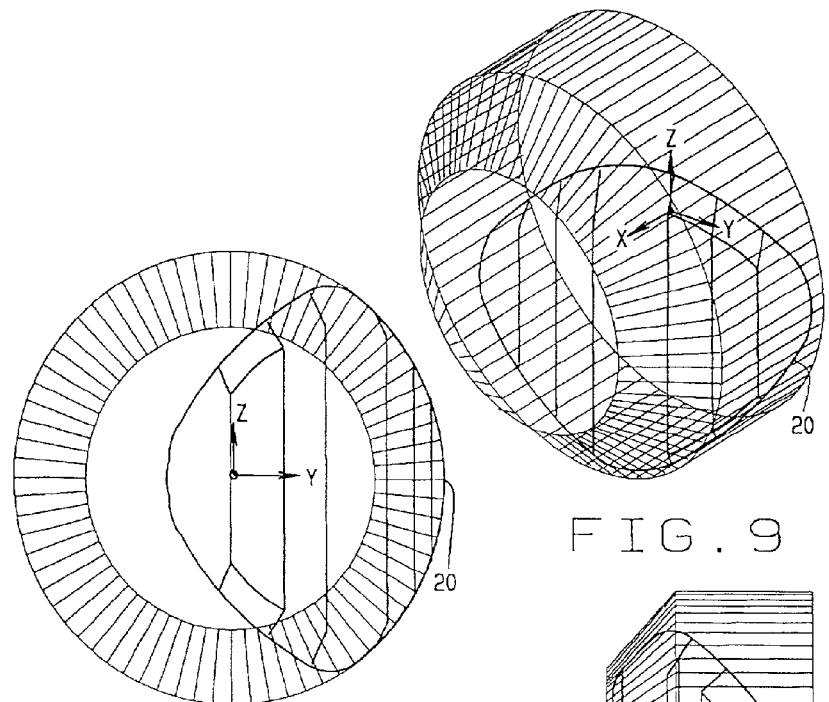
FIG.9
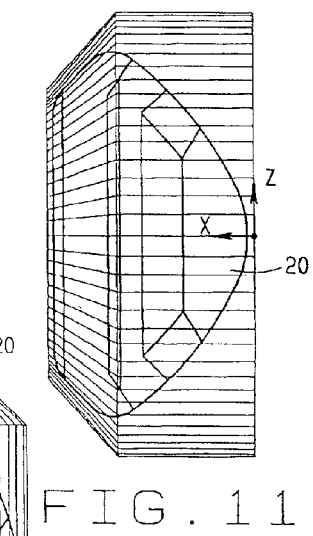
FIG.11
FIG.10
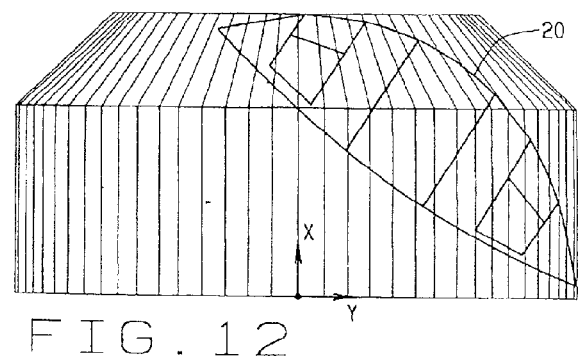
FIG.12

US 6,975,197 B2

ROTATING AND PIVOTING MAGNET FOR MAGNETIC NAVIGATION

FIELD OF THE INVENTION

This invention relates to magnet medical procedures, and in particular to a magnet useful in navigating magnetic medical devices in the body.

BACKGROUND OF THE INVENTION

Electromagnets and permanent magnets have been developed for moving magnet medical devices in the body. Some magnets used in medical applications apply a gradient to pull magnet medical devices within the body. Other magnets used in medical applications simply apply a magnetic field in a selected direction to align magnetic medical devices in the selected direction. Still other magnets apply both a magnetic field and a magnetic gradient to simultaneously orient and move a magnetic medical device.

There are a number of important competing design considerations for magnets used in medical procedures. First and foremost is providing sufficient field strength or gradient to orient or move the magnetic device. Electromagnets and in particular superconducting electromagnets can create strong magnet fields and gradients, but they are expensive to construct and operate. Until recently, it was difficult to construct a permanent magnet that could provide a sufficiently strong and universally directed magnetic field and gradient at a distance sufficiently far from the magnet to be useful in medical procedures. Recently, a focused permanent magnet has been developed which can create useful magnet fields at sufficient distances from the magnet to be employed in magnet surgery. The magnet is comprised of a plurality of segments each magnetized in a direction to contribute to the desired magnetic property, for example field strength at an operating point spaced in front of a magnet. This magnet and its method of design are disclosed in copending, co-owned, U.S. patent application Ser. No. 09/546,840, filed Apr. 11, 2000, U.S. patent application Ser. No. 09/497,467, filed Feb. 3, 2000, the disclosures of which are incorporated herein by reference. This magnet has other useful properties in that field direction could be changed by a simple translation of the magnet. However, these magnets still had relatively large exclusion zones to accommodate the movement of the magnet. The large exclusion zone made access to the patient, and positioning of other medical equipment (particularly imaging equipment) in the procedure room difficult. Thus a second design criteria is to minimize the exclusion zone, to provide greater access to the patient for medical staff and equipment.

A third design criteria is to minimize the degrees of freedom of magnet motion to provide a universally directed magnetic field. The fewer degrees of freedom of magnet motion needed, the simpler the navigation, and the less expensive the apparatus for moving the magnet.

SUMMARY OF THE INVENTION

The present invention relates to a magnet, and to a magnet system that is capable of generating useful magnet fields in virtually any direction, at distances from the magnet sufficient to conduct medical procedures in the patient's body. The magnet is designed so that a magnetic field can be generated in virtually any direction with a minimum amount of movement so that the exclusion zone—the zone from which the patient and other medical equipment and personnel cannot be located—or the inclusion zone—the zone that the magnet occupies—is minimized.

Generally the magnet of the present invention comprises a plurality of magnet segments each magnetized in direction to optimize the magnetic field at an operating point spaced from the magnet. The magnet is adapted to pivot about a first axis spaced behind the magnet, and to rotate about a generally horizontal axis. Through a combination of pivoting and rotating the magnet can project a magnetic field at the operating point in virtually any direction of sufficient strength to be useful. The shape of the magnet is determined to minimize the inclusion zone, which in the preferred embodiment is a horizontal cylinder, with a beveled edges on the forward face.

BRIEF DESCRIPTION OF THE DRAWINGS

FIG. 5 is a perspective view of the inclusion volume of a magnet constructed according to the principles of this invention, showing the magnet generally centered within the inclusion volume;

FIG. 6 is a front elevation view of the exclusion volume with the magnet in its centered position;

FIG. 7 is a right side elevation view of the exclusion volume with the magnet in its centered position;

FIG. 8 is a top plan view of the exclusion volume with the magnet in its centered position;

FIG. 9 is a perspective view of the inclusion volume, with the magnet pivoted to the left about the z axis;

FIG. 10 is front elevation view of the inclusion volume of the magnet, with the magnet pivoted to the left;

FIG. 11 is a right side elevation view of the inclusion volume, with the magnet pivoted to the left;

FIG. 12 is a top plan view of the inclusion volume, with the magnet pivoted to the left;

DETAILED DESCRIPTION OF THE PREFERRED EMBODIMENT

Figure 1A:
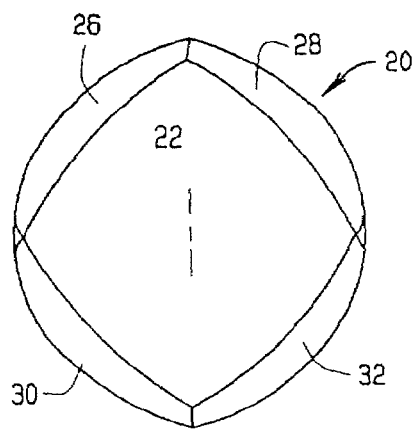
FIG. 1A is a front elevation view of a magnet constructed according to the principles of this invention.
Figure 1B:
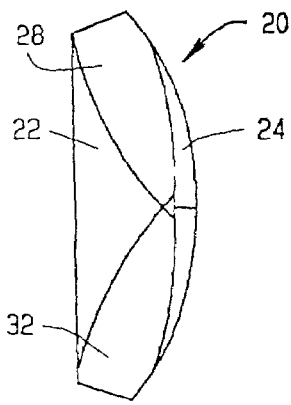
FIG. 1B is a right side elevation view of the magnet.
Figure 1C:
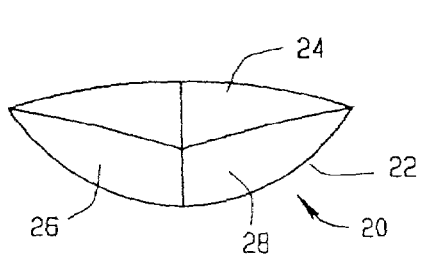
FIG. 1C is a top plan view thereof.
Figure 1D:
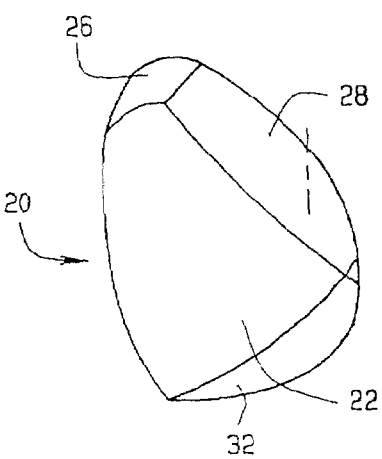
FIG. 1D is a front perspective view thereof.
Figure 1E:
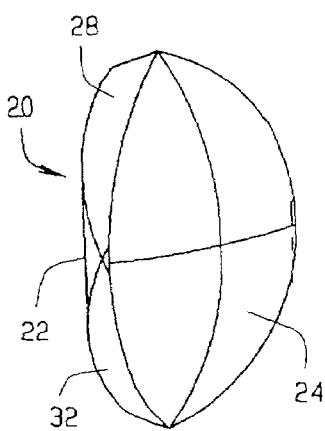
FIG. 1E is a rear perspective view thereof.

A magnet constructed according to the principles of this invention is indicated generally as 20 in FIGS. 1A through 1E. The magnet 20 comprises a generally cylindrical front face 22 and a back face 24. There are left top face 26 and a right top face 28, and a left bottom face 30 and a right bottom face 32. The magnet 20 preferably comprises a plurality of parallel bands or segments of permanent magnetic material extending from top to bottom. The magnetization direction of each segment is preferably selected to generally optimize the magnet field at a magnet operating point spaced from the center of the front face of the magnet. This magnet operating point is a design criteria of the magnet. For applications where a magnet field is to be applied relatively close to the magnet, such a neurology applications, the magnet operating point may be selected closer to the surface of the magnet, for applications where a magnetic field is to be applied relatively far from the magnet, such as cardiac applications, the magnet operating point may be selected further from the surface of the magnet. In this preferred, embodiment the magnet operating point is 13 inches from the center of the front face of the magnet. This represents a reasonable compromise to provide a magnet useful for both neurology and cardiac applications. Of course, the magnet could be optimized for some other operating point closer to or further from the front face of the magnet.

Figure 2A:
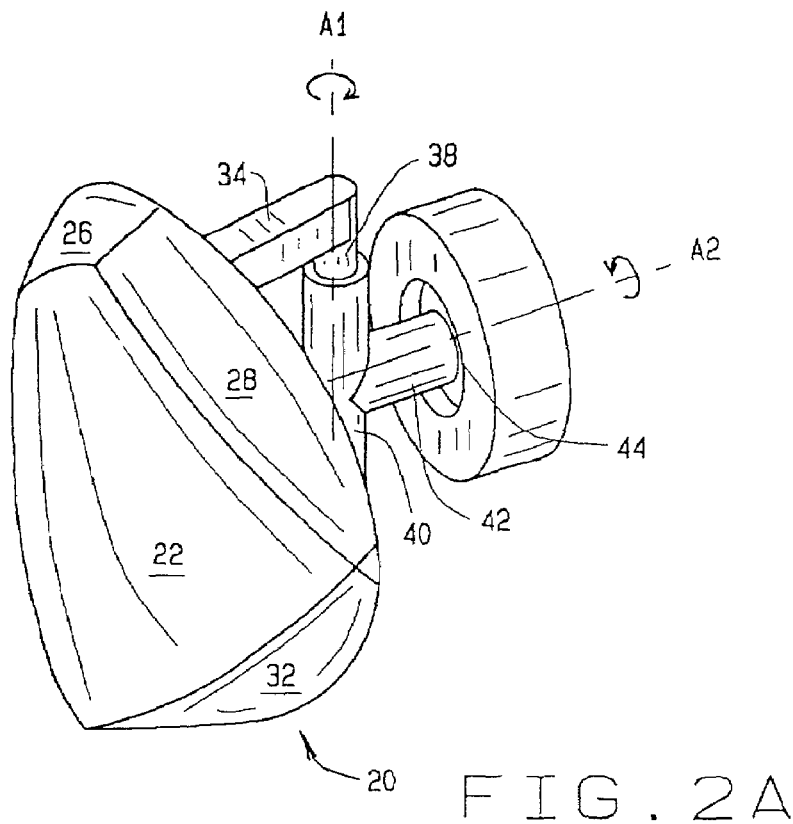
FIG. 2A is a perspective view of a support for pivoting and rotating a magnets in accordance with the principles of this invention, with the magnet in a first position.
Figure 2B:
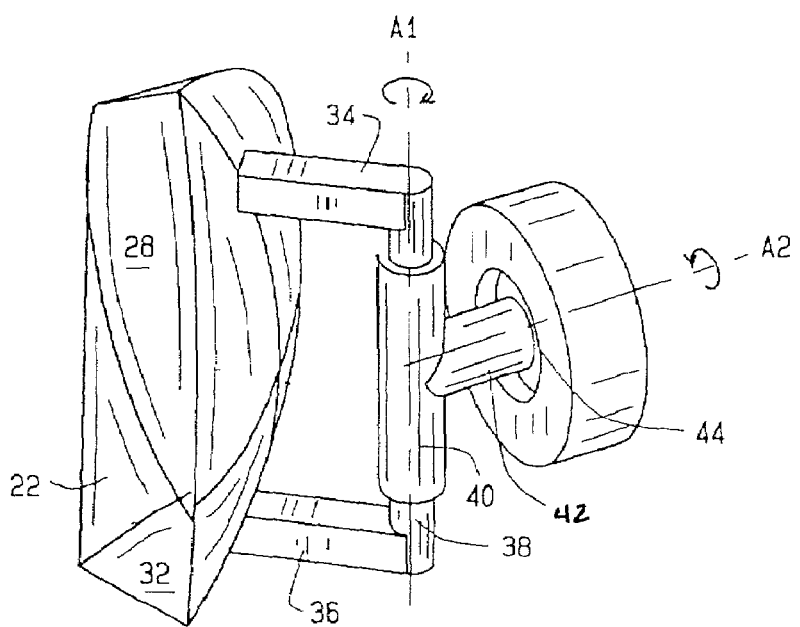
FIG. 2B is a perspective view of a support for pivoting and rotating a magnets in accordance with the principles of this invention, with the magnet pivoted to a second position.
Figure 3A:
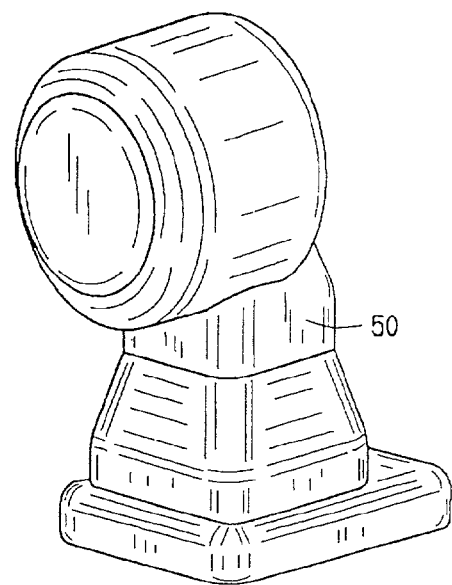
FIG. 3A is a perspective view of a housing containing the magnet and support.
Figure 3B:
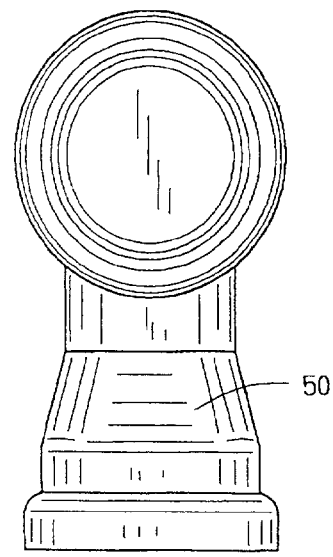
FIG. 3B is a front elevation view of the housing.
Figure 3C:
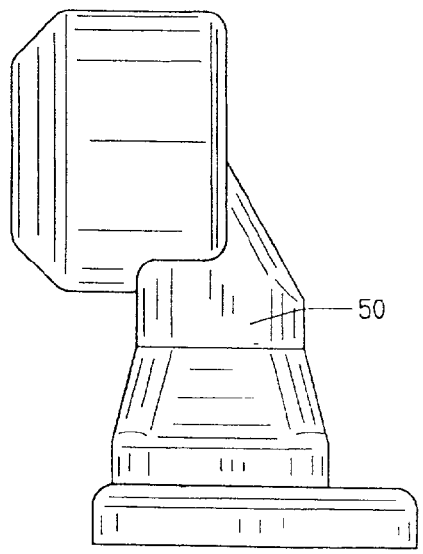
FIG. 3C is a right side elevation view of the housing.
Figure 3D:
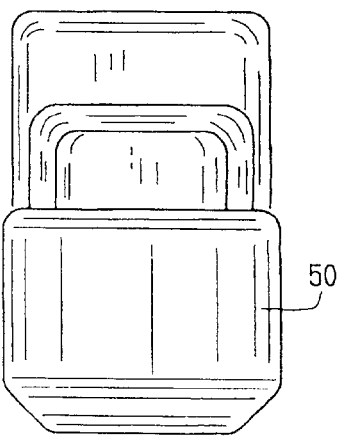
FIG. 3D is a top plan view of the housing.
Figure 4A:
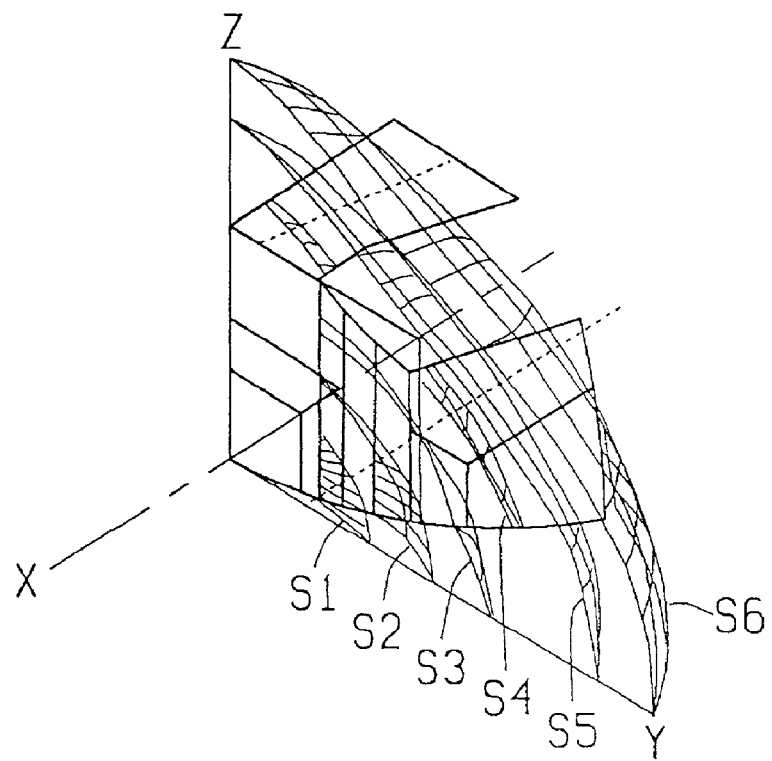
FIG. 4A is a perspective view of one quadrant of a magnet block, with several surfaces of equal contribution (represented in wire frame) superposed thereon.
Figure 4B:
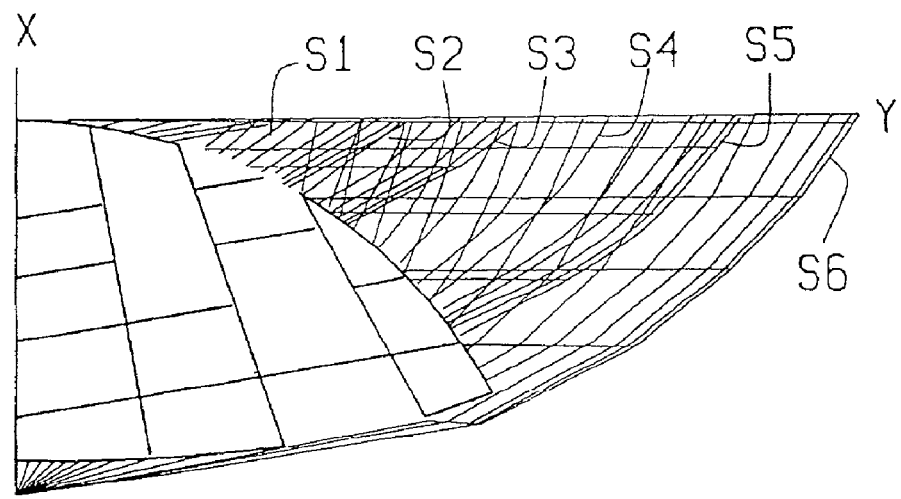
FIG. 4B is a top plan view of one quadrant of a magnet block with several surfaces of equal contribution.
Figure 4C:
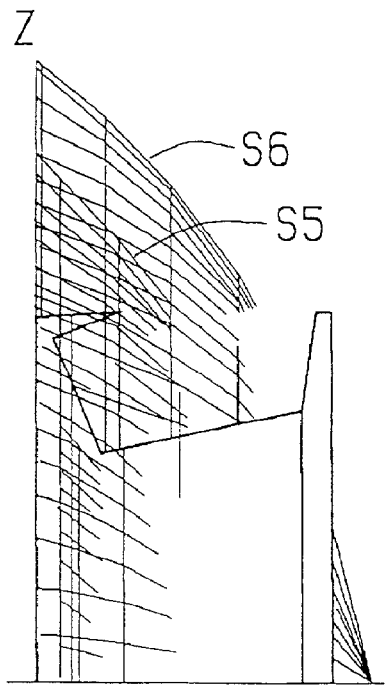
FIG. 4C is a right side elevation view of one quadrant of a magnet block with several surfaces of equal contribution.
Figure 4D:
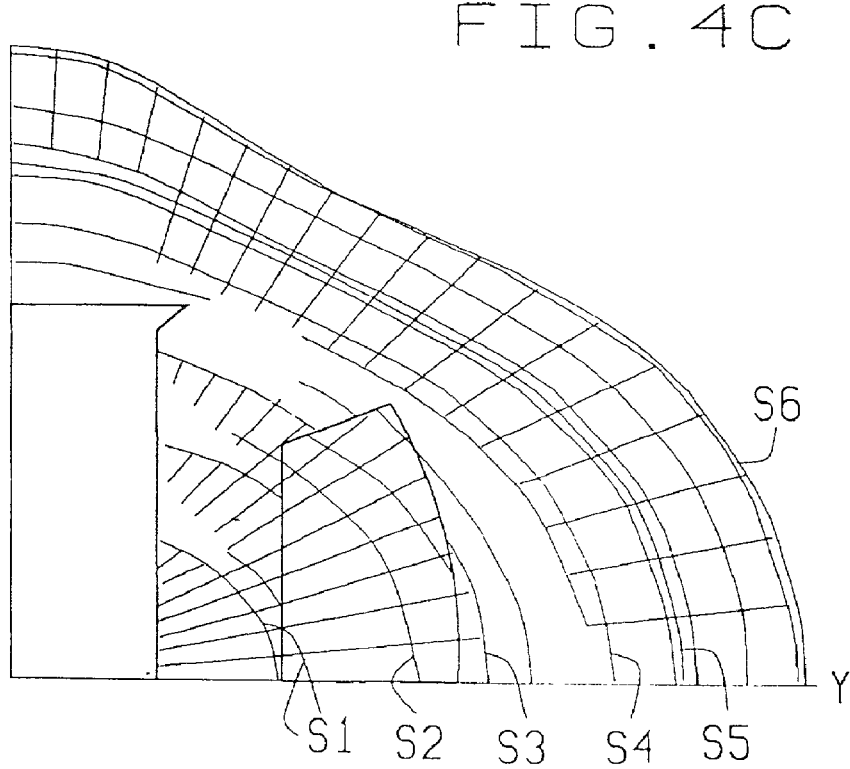
FIG. 4D is a rear elevation view of one quadrant of a magnet block with several surface of equal contribution.

The magnet 20 is preferably mounted for pivoting about a first axis A1, generally parallel to the vertical axis of the magnet. As shown in FIGS. 2A and 2B, upper and lower arms 34 and 36 project from the back surface 24 of the magnet 20. A cylindrical post 38 extends between the arms 34 and 36, and is journaled in a sleeve 40. The magnet is preferably also mounted for rotation about a second axis A2, that is generally horizontal, and that is perpendicular to, and intersects with, axis A1. As shown in FIGS. 2A and 2B, a sleeve 42 extends perpendicularly to sleeve 40, and is journaled around a horizontal arbor 44. Of course any other mechanism for mounting the magnet 20 to pivot about a first axis, and rotate about a second axis, and in particular to pivot about a first axis that rotates about a second axis can be used. In the preferred embodiment the axis A1 is fifteen inches from the front face of the magnet 20

A housing 50 for containing the magnet and structure for pivoting and rotating the magnet is shown in FIGS. 3A through 3D. The housing 50 contains the magnet and mechanism so that it is isolated from the procedure. Furthermore, the housing 50 eliminates moving parts from the procedure site, so that the system is less intimidating to the patients, and does not present any hazard to anyone at the procedure site. The housing 50 accommodates the inclusion zone of the magnet 20.

As described above, the magnet 20 is adapted to pivot about an axis A1 generally behind the magnet. The radius of curvature of the generally cylindrical front face 22 corresponds to the distance between the front face and the pivot axis (15inches in this preferred embodiment). The back face of the magnet is shaped in accordance with a surface of constant contribution to the magnetic field at the operating point. Material on such a surface contributes equally to the magnetic field at the operating point, regardless of its position on the surface. By selecting the appropriate surface of constant contribution to achieve the desired magnet size and strength, an excluding material that would lie beyond the surface, the weight of the magnet can be optimized for its selected magnetic properties. A constant contribution force can be calculated or plotted by maximizing the contribution to a particular magnet property at the magnet's operating point, for example the transfer field at the magnet's operating point, and determining the surface of points that contribute equally to the selected magnetic property. The superposition of several such surfaces df constant contribution is shown in FIGS. 4A through 4D. As shown in FIGS. 4A to 4D, various surfaces of constant contribution $S_1$, $S_2$, $S_3$, $S_4$, $S_5$, and $S_6$, are shown, and the final shape of back side of the magnet is determined based upon t constant contribution surface that leaves sufficient magnetic material to achieve the desired field strength, gradient, or field gradient product, while keeping the weight low. It is desirable to keep the weight of the final magnet low both to conserve magnetic material, which can be expensive, and to reduce the structural requirements for the supporting mechanism for the magnet. Because of limitations of manufacturing magnets with smooth continuously curved surfaces, the actual shape of the back surface may only approximate the shape of the constant contribution surface. In the preferred embodiment, the magnet is capable of producing a field of at least about 0.4 T at an application point at least 13inches from the surface of the magnet, or about 0.1 T at an application point of 7.5 inches from the surface of the magnet, yet weights less than about 500 pounds.

An important design criteria for the magnet 20 is its inclusion volume, which represents the combination of all of the volumes that the magnet occupies throughout all of the desired possible orientations of the magnet, i.e., all of the desired pivots and rotations. The inclusion volume of a magnet constructed according to the principles of this invention is shown in FIGS. 5 through 8, with the magnet in a first position within its exclusion zone, and in FIGS. 9 through 12 with the magnet 20 in a second position within its exclusion zone, pivoted 35°, which because of the design of the magnet described above, results in a magnetic field direction shift of 90° at the system's operation point. The system's operation point is a design element, and in this preferred embodiment is thirteen inches from the center of the front face of the inclusion volume, which corresponds to thirteen inches from the center of the front face of the housing 50. The magnet's operation point and the system's operation point correspond when the magnet 20 is in its centered position in its exclusion zone. In the preferred embodiment the pivot point is 15 inches behind the front face of the magnet, and 28 inches (15 plus 13 inches) behind the operating point. As shown and described in the Figures, the pivot point is generally horizontal, and extends through the pivot axis. In this preferred embodiment, the inclusion volume is generally cylindrical, with a beveled forward edge. The inclusion volume has a diameter of about 30 inches and a depth of about 14 inches. The bevel on the forward face of the volume is at approximately 45°, to a depth of about 5 inches, so that the diameter of the generally circular front face is about 20 inches. The edge of the magnet 20 is shaped so that the magnet 20 remains within the exclusion volume.

Two magnets 20 can be mounted in opposition, so that their magnetic fields add, to provide a useful magnetic field at greater distances, for example to conduct cardiac procedures in the chest, where the application point of the magnetic field is necessarily far away from the magnet.

Figure 13:
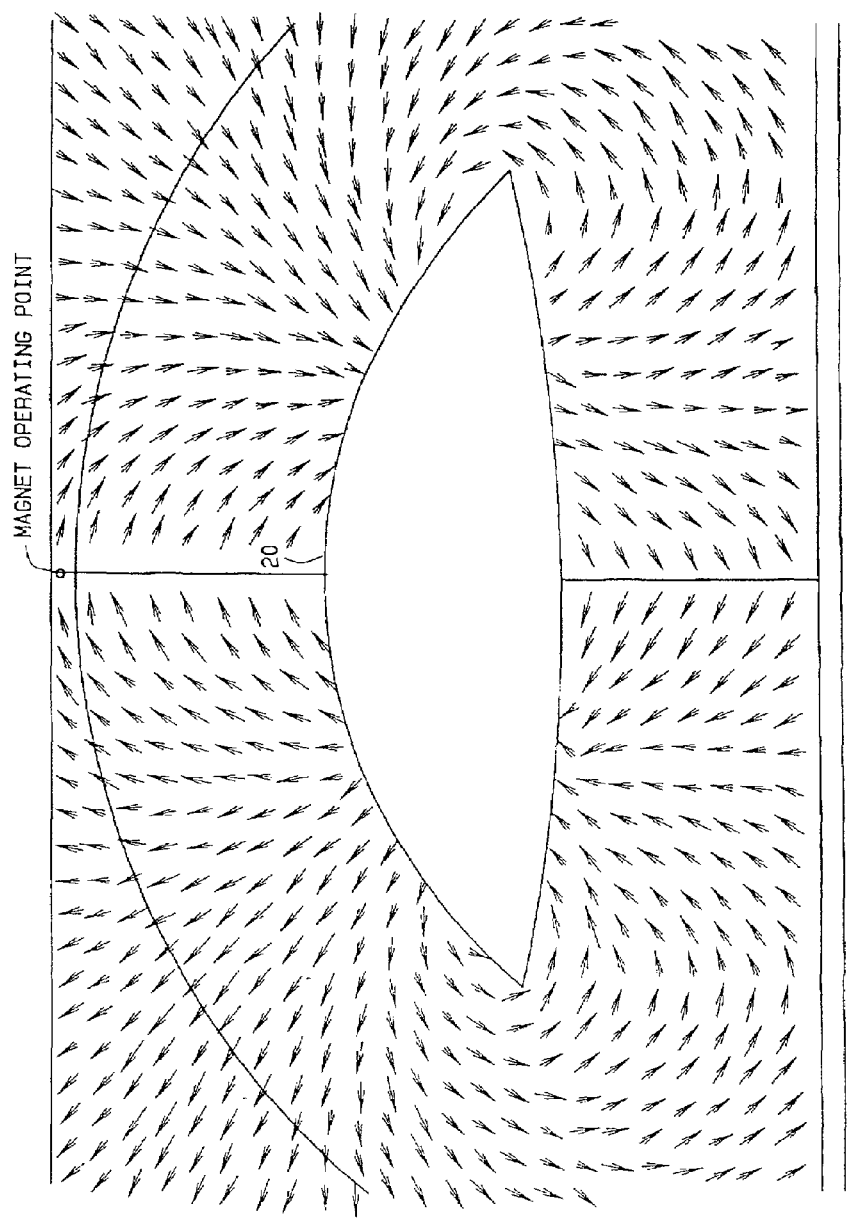
FIG. 13 is a top plan view of a magnet constructed according to the principles of this invention, showing the local magnetic field directions in the space surrounding the magnet.

As shown in FIG. 13, when the magnet 20 is in its centered position, it produces a transverse magnetic field at an operating point at the front of the magnet assembly. Rotation of the magnet 20 approximately 35° clockwise about an axis parallel to the longitudinal axes of the magnetic segments results in a magnetic field at the operating point at the front of the magnet assembly to point outwardly, away from the magnetic assembly, and rotation of the magnet approximately 35° counterclockwise about that axis results in a magnetic field at the operating point at the front of the magnet assembly to point inwardly, into the magnetic assembly. Thus over the span of a mere 70° of pivoting, the magnetic field direction changes 180°. This pivoting, combined with rotation of the magnet about the second axis, allows the magnet to create a magnetic field in any direction at the operating point of the assembly, through a simple pivoting and rotation of the magnet, without translation. Thus the inclusion volume of the magnet can be made very small, which means that exclusion volume is small, and access to the patient by health care professionals and medical equipment is not impaired.

Figure 14:
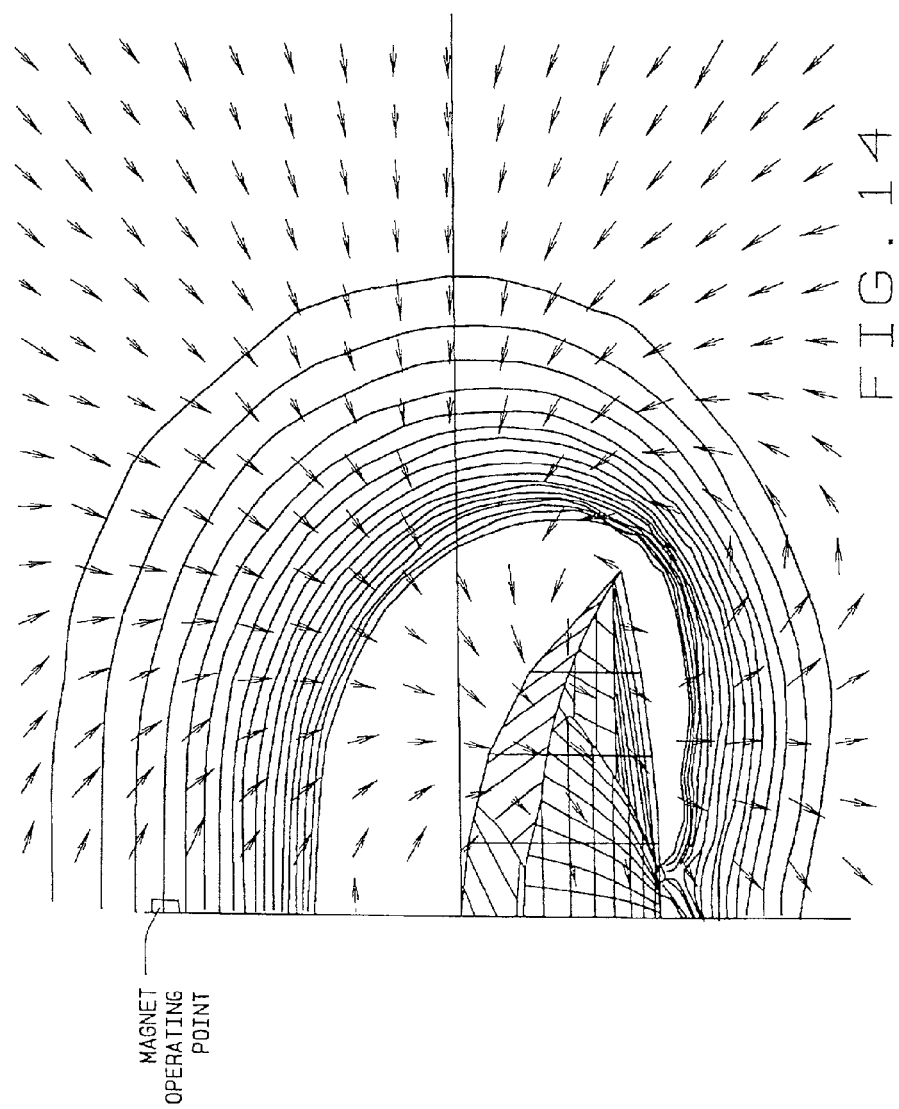
FIG. 14 is a horizontal cross sectional view of one half of a magnet constructed according to the principles of this invention (the other half being a mirror image thereof), showing the magnetization directions of the segments comprising the magnet, and the local field directions surrounding the magnet and lines of constant magnetic field strength.
Figure 15:
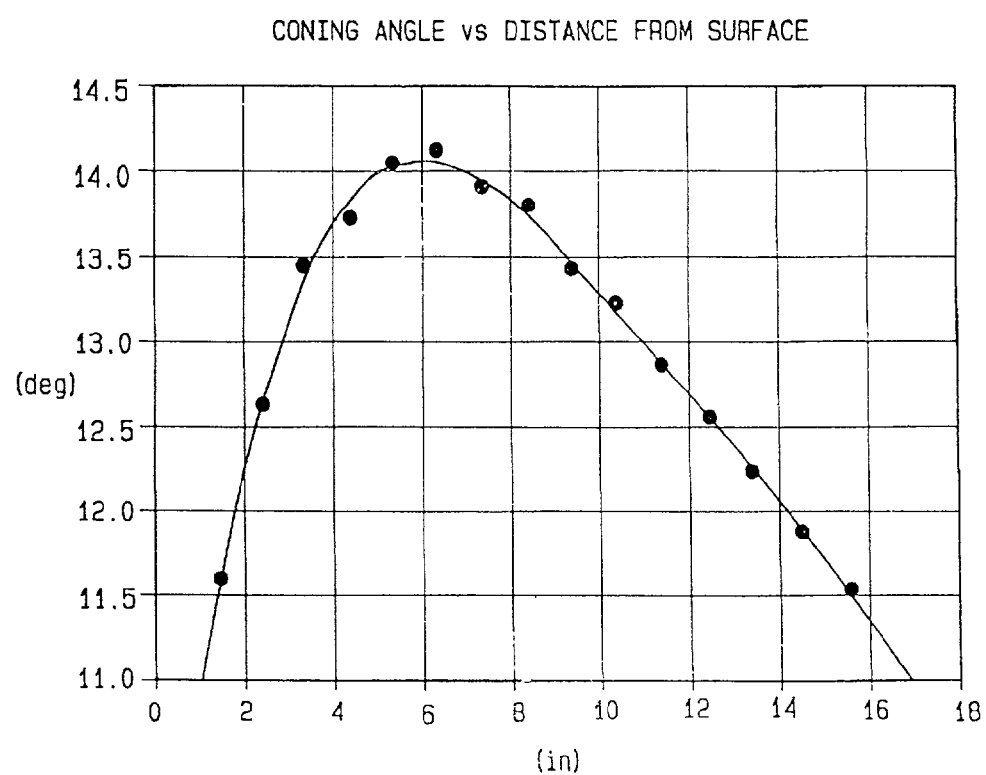
FIG. 15 is a graph of maximum coning angle versus distance from the magnet.

While it is possible with the magnet assembly of the present invention to project a field at the application point in any direction, at sufficient strength to be useful, it may not always be possible to move smoothly and continuously from one magnetic field direction to another in the plane containing both directions. Thus when changing the field from a first direction to the second direction, it is possible that a field direction will temporarily swing out of the plane—a phenomenon known as coning. However, amount of coning depends upon the distance from the magnet, and as shown in FIG. 14, the maximum coning is slightly more than 14° from the desired plane, and occurs at distances of about six inches from the magnet. At a distance of 12 inches from the magnet, the maximum coning is about 12.75°.

Figure 16:
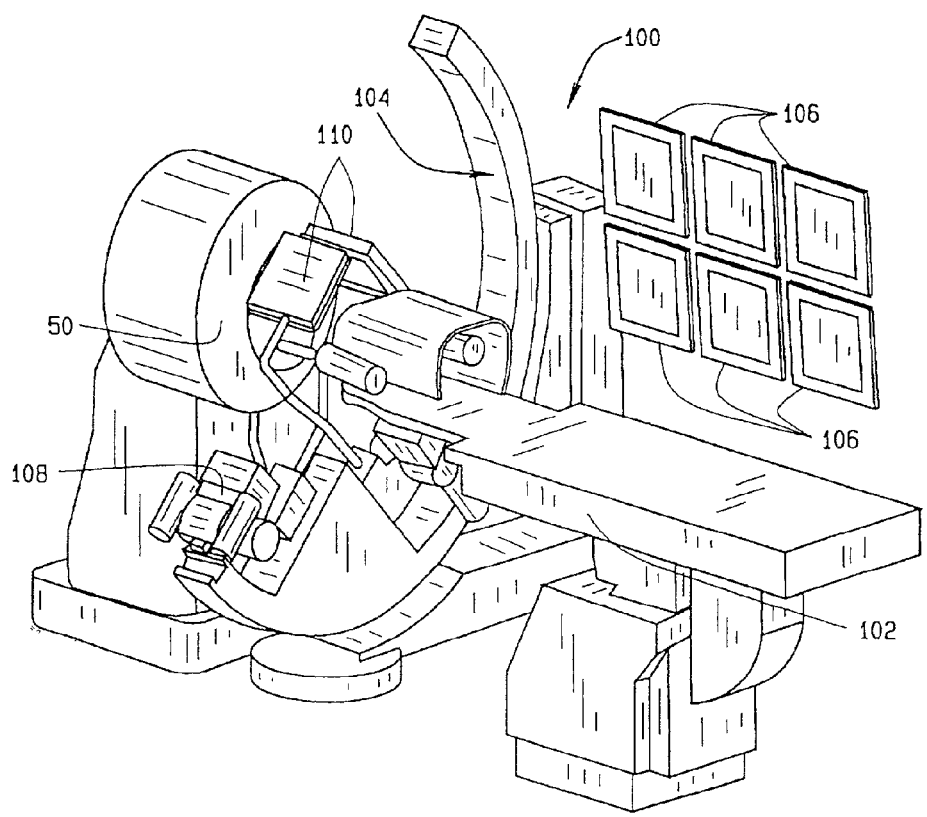
FIG. 16 is a perspective view of a magnetic surgery system incorporating a magnet constructed according to the principles of this invention.

A magnetic surgery system incorporating a magnet system constructed according to the principles of the present invention is indicated generally as 100 in FIG. 16. The system 100 includes a magnet 20 and its support and moving structure contained within a housing 50. The system 100 is particularly adapted for conduct neurological procedures, and the housing is positioned to be near the patient's bead, in this case at the top of the patient's head. The system 100 includes a patient support, such a patient bed 102, which may or may not be movable. A C-arm 104 mounts bi-planar imaging equipment for making bi-planar images of the procedure site, and displaying them on the displays 106. The bi-planar image equipment includes an imaging beam sources, such as x-ray sources 108, and imaging beam receivers or detectors, such as amorphous silicon last plates 110, which are substantially unaffected by the presence of magnetic fields. The magnet 20 inside the housing 50 can be used to navigate a magnetic medical device in the patients head by pivoting the magnet about axis A1and rotating the magnet about axis A2 to achieve the desired magnetic field to orient a magnetic medical device inside the patient's head. The bi-planar imaging allows the physician and other health care workers to monitor the orientation and position of the magnetic medical device to navigate the distal end of the magnetic medical device to its desired destination. While the magnet assembly is designed to apply a magnet field at the systems' operating point, which, as described above is a point thirteen inches from the front face of the housing 50, the system preferably allows the application of a magnetic field in virtually any direction in sufficient strength for navigation purposes, e.g. 0.1 T, anywhere in 7 inch diameter cylinder surrounding the line from the center of the front face of the housing to the system's operating point.

Figure 17:
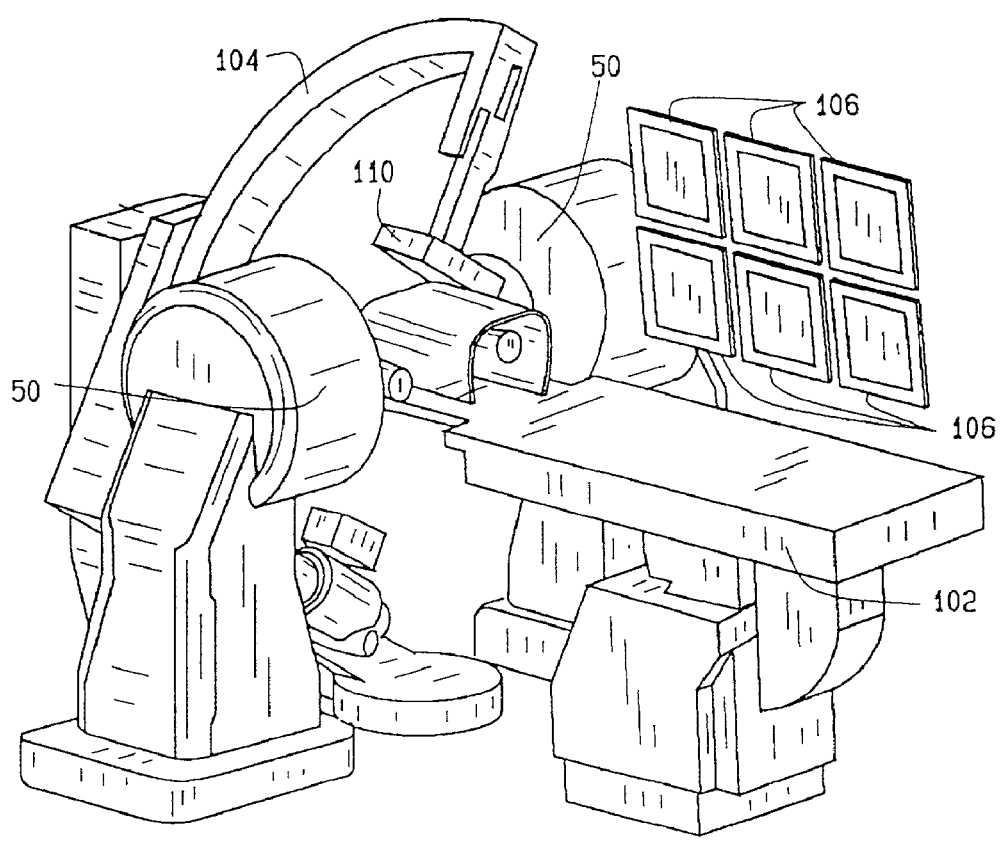
FIG. 17 is a perspective view of a magnetic surgery system incorporating two magnets constructed according to the principles of this invention.

A magnetic surgery system incorporating two magnet systems constructed according to the principles of the present invention is indicated generally as 200 in FIG. 17. The system 200 includes two magnets 20 and their respective support and moving structures, each contained within a housing 50. The housings 50 are disposed on opposite sides of the patients, so that the operating points of each magnet system overlap so that the magnetic fields produced by the two systems are additive. The system 200 is particularly adapted for cardiac procedures, and the housings 50 are positioned on opposite sides of the patient's chest. The system 200 includes a patient support, such a patient bed 202, which may or may not be movable. A C-arm 204 mounts bi-planar imaging equipment for making bi-planar images of the procedure site, and displaying them on the displays 206. The bi-planar image equipment includes an imaging beam sources, such as x-ray sources 208, and imaging beam receivers or detectors, such as amorphous silicon last plates 210, which are substantially unaffected by the presence of magnetic fields. The magnets 20 inside the housing 50 can be used to navigate a magnetic medical device in the patient's head by pivoting the magnet about axis A1 and rotating the magnet about axis A2 to achieve the desired magnetic field to orient a magnetic medical device inside the patient's head. The bi-planar imaging allows the physician and other health care workers to monitor the orientation and position of the magnetic medical device to navigate the distal end of the magnetic medical device to its desired destination. While the magnet assembly is designed to apply a magnet field at the systems' operating point, which, as described above is a point thirteen inches from the front face of the housing 50, the system preferably allows the application of a magnetic field in virtually any direction in sufficient strength for navigation purposes, e.g. 0.04 T, anywhere in 7 inch diameter circle thirteen inches from the front face of the housing.

What is claimed:

1. A magnet assembly comprising a magnet composed of a plurality of segments, each segment having a magnetization direction that optimizes the magnetic field in a selected direction at an operating point in front of the assembly and so that the pivoting of the magnet about an axis behind the magnet through an arc of less than 90° causes the magnetic field direction at the operating point to vary by 180°.

2. A magnet assembly comprising a magnet mounted for pivoting about a first axis spaced from the magnet, and rotating about a second axis that is perpendicular to and intersects with the first axis, the magnet comprising a plurality of segments, each segment having a magnetization direction so that the pivoting of the magnet about the first axis through an arc of less than 90° causes the magnetic field direction created by the magnet at an operating point spaced from the magnet to vary by 180°.

3. A magnet assembly comprising a magnet mounted for pivoting about a first axis spaced from the magnet, and rotating about a second axis that is perpendicular to and intersects with the first axis, the magnet comprising a plurality of segments each with a magnetization direction such that through a combination of pivoting and rotating the magnet projects a magnetic field in any direction at an operating point spaced from the front of the assembly.

4. The magnet assembly according to claim 3 wherein the operating point is at least 12 inches from the magnet assembly.

5. The magnet assembly according to claim 3 wherein the assembly can project a magnetic field at the operating point of at least 0.04 T in any direction.

6. The magnet assembly according to claim 3 wherein the assembly can project a magnetic field at the operating point of at least 0.1 T in any direction.

7. In combination, first and second magnet assemblies disposed on opposite sides of a patient, each magnet assembly comprising a magnet mounted for pivoting about a first axis spaced from the magnet, and rotating about a second axis that is perpendicular to and intersects with the first axis, the magnet comprising a plurality of segments each with a magnetization direction such that through a combination of pivoting and rotating the magnet projects a magnetic field in any direction at an operating point spaced from the front of the assembly.

8. The magnet assembly according to claim 3 wherein the segments of the magnet are magnetized in directions such that the pivoting of the magnet about the first axis through an arc of less than 90° causes the magnetic field direction created by the magnet at the operating point to vary by 180 90°.

9. The combination according to claim 7 wherein the segments of each magnet are magnetized in directions such that the pivoting of the magnet about the first through an arc of less than 90° causes the magnetic field direction created by the magnet at the operating point to vary by 180 90°.

10. The combination according to claim 7 wherein the operating point is at least 12 inches from the magnet assembly.

11. The combination according to claim 7 wherein each assembly can project a magnetic field at the operating point of at least 0.04 T in any direction.

12. The combination according to claim 7 wherein the assemblies together can project a magnetic field at the operating point of at least 0.1 T in any direction.

* * * * *